(12) United States Patent
Freund et al.

(10) Patent No.: US 6,712,769 B2
(45) Date of Patent: Mar. 30, 2004

(54) BLOOD PRESSURE MONITORING DEVICE WITH INCLINATION SENSOR

(75) Inventors: Dirk Freund, Kelkheim (DE); Martin Giersiepen, Oberursel (DE); Brigitte Harttmann, Niedernhausen (DE); Ulrich Heck, Krefeld (DE); Stefan Hollinger, Kronberg (DE); Frank Kressmann, Schwalbach (DE); Gerrit Rönneberg, Darmstadt (DE); Fred Schnak, Kronberg (DE)

(73) Assignee: Braun GmbH (DE)

( * ) Notice: Subject to any disclaimer, the term of this patent is extended or adjusted under 35 U.S.C. 154(b) by 44 days.

(21) Appl. No.: 10/183,856

(22) Filed: Jun. 25, 2002

(65) Prior Publication Data

US 2003/0013976 A1 Jan. 16, 2003

Related U.S. Application Data

(63) Continuation of application No. PCT/EP00/11769, filed on Nov. 25, 2000.

(30) Foreign Application Priority Data

Dec. 29, 1999 (DE) .......................... 199 63 633

(51) Int. Cl.⁷ ........................ A61B 5/02; A61B 5/103; A61B 5/117
(52) U.S. Cl. ................. 600/503; 600/485; 600/595
(58) Field of Search ................. 600/503, 502, 600/501, 500, 485, 483, 481, 490, 587, 595, 493

(56) References Cited

U.S. PATENT DOCUMENTS

| 5,042,505 A | 8/1991 | Mayer et al. |
| 5,574,442 A | 11/1996 | Kinoshita et al. |
| 5,778,879 A | 7/1998 | Ota et al. |

FOREIGN PATENT DOCUMENTS

| DE | 29612412 U1 | 10/1996 |
| DE | 19757974 A1 | 7/1999 |
| RU | 1825091 | 6/1996 |
| WO | WO 99/33395 | 7/1999 |

*Primary Examiner*—Max F. Hindenburg
*Assistant Examiner*—Navin Natnithithadha
(74) *Attorney, Agent, or Firm*—Fish & Richardson PC

(57) ABSTRACT

The invention is directed to a wrist blood pressure monitoring device comprising a pressure sensor for detecting a pressure signal, an applicator unit for applying the pressure sensor against the wrist area of a subject's lower arm, an evaluating unit for evaluating the pressure signal, and an inclination detecting device for detecting the inclination of the blood pressure monitoring device and for delivering an electrical inclination signal corresponding to the inclination. According to the invention, the inclination detecting device comprises at least one movable, in particular pendulum-type positioning element and an inclination sensing device cooperating with the positioning element and including at least one sensing element movable with the positioning element and formed in particular by an optically reflecting, wedge-shaped arc section of the positioning element, and at least one further sensing element having in particular a reflected light barrier. The sensing elements are configured such that the electrical inclination signal is derivable from the relative position of the relatively movable sensing elements.

33 Claims, 4 Drawing Sheets

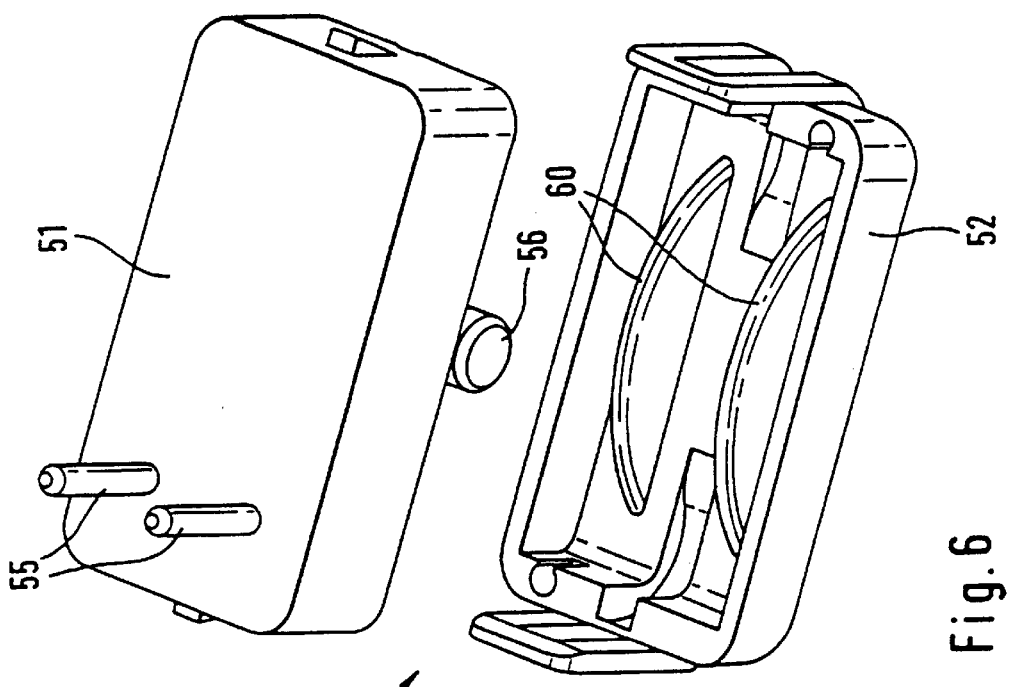
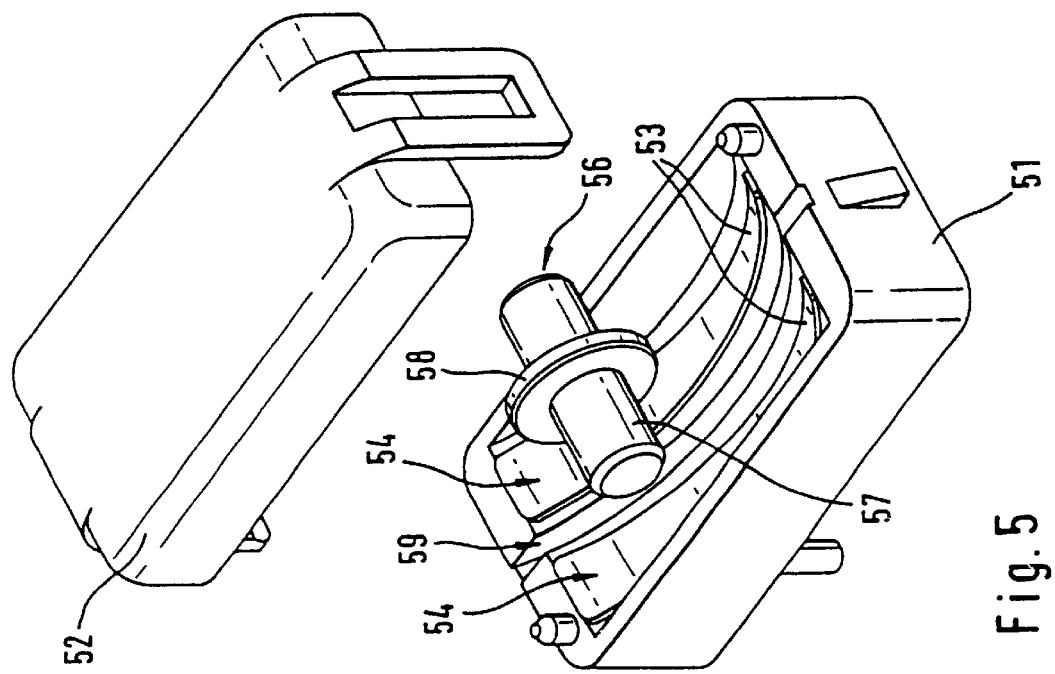

BLOOD PRESSURE MONITORING DEVICE WITH INCLINATION SENSOR

This is a continuation of PCT application Ser. No. PCT/EP00/11769, filed Nov. 25, 2000, which claims priority from German application serial number 19963633.8, filed Dec. 29, 1999.

This invention relates to a blood pressure monitoring device according to the prior-art portion of claim 1.

Blood pressure monitoring devices of this type include integrated in a housing a display device for indicating the blood pressure measurement values, a control device for controlling the individual components of the blood pressure monitoring device, a power source, a pumping device, and a valve for controlled air inflation and deflation in the bladder of a cuff, a pressure sensor for detecting a pressure signal, an evaluating device for evaluating the pressure signal, and an inclination detecting device preferably arranged in the interior of a housing of the blood pressure monitoring device for detecting the inclination of the blood pressure monitoring device relative to the horizontal and for delivering an electrical inclination signal indicative of the inclination, and, disposed on the housing, an applicator unit for applying the pressure sensor against a subject's limb in the wrist area of his or her lower arm.

Blood pressure monitoring at a subject's wrist or finger frequently suffer from lack of measurement accuracy and insufficient repeatability. For one part, this may be attributable to the high sensitivity of the measurements to variations in the measuring position, that is, the individual position of the wrist or finger relative to the position of the heart. In the event of a measuring position deviating from heart level, the measurement result is corrupted by about 0.8 mm Hg/mm due to the hydrostatic pressure differential between the heart and the measuring position. An improper position during a measurement cycle hence produces a systematic measurement error.

Various proposals have been made in the past to obtain improved blood pressure readings in the light of these problems. In particular, proposals have been made to detect the inclination of the lower arm relative to the horizontal because this inclination, given a predetermined position of the elbow as, for example, a position in which it rests against the upper part of the body, is a measure of the level of the wrist and hence of the hydrostatic component of the blood pressure in the wrist area.

An inclination-sensing blood pressure monitoring device is described, for example, in DE 296 12 412 U1. Arranged in the interior of the housing of the blood pressure monitoring device is a disk-shaped pendulum whose circumference visible through a window in the housing is color-marked. This marking indicates an inclination range within which the blood pressure measurement values can be considered as sufficiently correct because the arm is held so that the wrist is positioned roughly at the level of the heart. Similar simple mechanical solutions are also described in Japanese Offenlegungsschrift JP-8-580 (Application Serial No. 6-145168) or in Japanese publication 09038055 A (Application Serial No. 07196590). The requirement for direct observability of the pendulum through the window disposed adjacent to the blood pressure value indicating device results in considerable overall sizes of such blood pressure monitoring devices. Furthermore, handling is rendered difficult because of the need for the pendulum to settle first before reliable readings can be obtained.

The art knows of blood pressure monitoring devices equipped with inclination detecting devices which are in a position to produce an electrical inclination signal which, also for reasons of greater ease of the further processing of electrical signals, is advantageous. Such a blood pressure monitoring device is disclosed, for example, in U.S. Pat. No. 5,778,879 which does not however provide any specifics as to the mode of operation of the inclination detecting device. Japanese Offenlegungsschrift 7-143970 (Application Serial No. 5-295062) describes a blood pressure monitoring device which uses as inclination sensor an electrolyte sensor, not described in greater detail, whose output voltage is varied in response to the inclination by variation of the resistance value. Such sensors require elaborate sealing and should operate on A.C. voltage to avoid changes in the composition of the electrolyte, which again necessitates a substantial control effort.

From U.S. Pat. No. 5,042,505 an electronic sensing device is known in which the change of an angular position relative to a first angular position of the human spinal column can be measured. To this effect, provision is made for an optical encoder with a movable pendulum unit whose degree of rotation up to 360° is determinable in a digital electrical signal in the form of electrical pulses per angular degree of rotation of the pendulum. This known inclination detecting device thus comprises a movable positioning element and an inclination sensing device cooperating with the positioning element, which includes at least one sensing element movable with the positioning element and at least one further sensing element, said sensing elements being configured such that the electrical inclination signal is derivable from the relative position of the relatively movable sensing elements.

From SU 1825091 an inclination sensor for measuring rails is known. The inclination measurement supplies a relative signal formed by the position of a pendulum with inductive measuring unit.

From U.S. Pat. No. 5,574,442 an inclination sensor with a movable electrode engaging between two fixed electrodes is known. The movable electrode produces an electrical capacitance between the two other electrodes which varies with the angle of inclination.

A blood pressure monitoring device of the type initially referred to is known from DE 197 57 974 A1.

It is an object of the present invention to provide a blood pressure monitoring device of the type indicated in the prior art portion, which is equipped with an inclination detecting device for delivering an electrical inclination signal, said detecting device being of straightforward construction and operating accurately and reliably.

To accomplish this object, the present invention proposes a blood pressure monitoring device incorporating the features of claim 1.

In blood pressure monitoring devices of the invention, the inclination detecting device comprises at least one movable positioning element and an inclination sensing device cooperating with the positioning element and including at least one first sensing element movable with the positioning element and at least one second sensing element movable relative to the first sensing element, said sensing elements being configured such that the electrical inclination signal is derivable from the relative position of the relatively movable sensing elements. In this arrangement, the positioning element is understood to be a movable member which, in relation to the gravity vector, that is, in relation to the vertical, attempts to occupy invariably the same position of equilibrium, with the inclination of the blood pressure monitoring device being a measure of the inclination of the lower arm. The positioning element may be formed, for example, of a liquid surface or a body floating on a liquid, whose alignment is dictated by the alignment of the liquid surface. The possibility also exists to configure the positioning element as a pendulum movable in one or several axes, that is, as a mass which is, for example, fixedly mounted on a housing outside its center of gravity. Positioning elements rolling off along curved surfaces or operating according to the gyroscopic principle may also be contemplated. The use of the relative movability of the sensing elements and the unambiguous relationship between inclination angle and equilibrium rest position afford the possibility of employing a plurality of preferably physical effects for generation of the inclination signal, utilizing in particular electric, electromagnetic and/or magnetic fields and/or electromagnetic and/or acoustic waves, as well as changes in capacitance resulting from position changes of capacitor surfaces.

The sensing element movable with the positioning unit can be coupled, for example, mechanically or through a field of force, to the movement of the positioning element. Preferably, this sensing element is fixedly connected with the positioning element and/or formed by part of the positioning element as, for example, a surface section thereof. The other sensing element can be fixedly connected with a housing of the blood pressure monitoring device or a mounting structure fixedly attached to the housing, as a card or printed circuit board carrying electronic components or a housing of the inclination detecting device. The relative motion then results from the movement of one sensing element with the blood pressure monitoring device, while the sensing element operatively coupled to the positioning unit maintains or attempts to occupy a position of equilibrium relative to the gravity vector. This arrangement in which the equilibrium relative position of the sensing elements is dictated by the angle of inclination of the blood pressure monitoring device or the subject's limb carrying it, can be utilized for generation of the inclination signal.

In a further aspect, at least one sensing element is formed by an arc section which is preferably curved uniformly or in the manner of a circular arc. The arc section can be essentially two-dimensional or three-dimensional in the form of a body. The other sensing element is arranged in the area of the arc section, either making contact therewith or being spaced therefrom in close proximity thereto. Depending on the position of the blood pressure monitoring device, a clearly position-related part or portion of the arc section is then operatively associated with the other sensing element so that the inclination signal is obtainable, for example, from a preferably continuous property change of the arc section in the direction of the arc. For example, a surface property of the arc section, as its surface-area-specific or integral reflecting power for optical radiation or light, can be subject to variation in the direction of the arc, and/or at least one dimension of the arc section, for example, its width, can be subject to variation in the arc direction. It is also possible to derive an inclination signal from an inclination-angledependent variation of the distance between the sensing elements as by configuring, for example, the arc section in such manner that its distance from the other sensing element is greater or smaller, depending on the angle of inclination.

In a preferred further aspect, one sensing element, in particular a sensor-active area or a sensor area effective in cooperation with the other sensing element, has a width varying in the direction of relative motion of the sensing elements or in the direction of the arc. This variation proceeds preferably linearly at least in sections, hence enabling an inclination signal to be produced which varies linearly with the inclination angle and lends itself to particular simple evaluation. Conveniently, a wedge or trapezoidal shape of the sensing element is provided for this purpose.

It is of particular advantage for the variation of a property of the arc section related to the direction of the arc or the direction of relative motion to proceed symmetrically relative to a reference position or zero position which corresponds, for example, to a horizontal alignment of the blood pressure monitoring device. In this manner no special evaluating effort is needed to produce an absolute signal for the inclination, and the blood pressure monitoring device can be used equally on either side of a patient's body. Where deemed necessary, further sensor arrangements may be provided to distinguish between upward and downward inclinations.

The concept of relatively movable, cooperating sensing elements can be made use of for producing the inclination signal in a variety of ways. In another aspect, the positioning element is of a pendulum-type configuration and mounted for rotation about an axis normally fixedly mounted on the housing, and one of the sensing elements is formed by an arc section arranged essentially concentrically with the axis of rotation, particularly by a peripheral section of the positioning element. The other sensing element is arranged preferably immovably in the area of the arc section. One of the advantages of using a peripheral section for forming a sensing element is that already at small angles of adjustment about the axis of rotation relatively large arc lengths can be utilized for signal generation, whereby the measurement accuracy can be enhanced. In yet another aspect, an arc section serving as sensing element is configured as a roll-off surface fixed to the housing and cooperates with another sensing element provided on a rolling member, said rolling member forming the positioning element. Roll-off contact between the sensing elements enables an easy, low-friction adjustment of the equilibrium of the positioning element in spite of relative contact of the sensing elements or the parts carrying them.

To produce the electrical inclination signal a variety of different effective relationships between the sensing elements can be utilized. In one embodiment the inclination sensing device is configured as an optically reflective inclination sensing device in which preferably one sensing element includes at least one reflecting surface for optical radiation while the other sensing element includes at least one source of radiation and at least one radiation detector, said reflecting surface being aligned relative to the radiation source and the radiation detector such that optical radiation from the radiation source which is reflected by the reflecting surface is incident on the radiation detector. For inclination-angle-dependent signal generation, for example, the surface-area-specific degree of reflection and/or the extension of the reflecting surface in the area of the radiation source and/or the radiation detector can vary in the direction of relative motion. Advantageously, the radiation source equipped, for example, with at least one light-emitting diode and the radiation detector equipped with at least one phototransistor or one photodiode may be integrated into a common component in the manner of a reflected light barrier. A preferred embodiment of this type will be explained later as the description proceeds.

It is also possible to configure the inclination sensing device as an optically transmissive inclination sensing device. This may equally include at least one radiation source or radiation emitter and at least one radiation detector or radiation receiver, which operate in a preferably similar region of the spectrum and are associated with one of the sensing elements. The other sensing element, particularly the one which is movable in response to gravity, may include an optically transmissive medium which exhibits a suitable absorption characteristic in this region of the spectrum and may be formed, for example, by a section of an arc or circumference of a pendulum or the like. The radiation source can radiate into the radiation receiver via an optical path either directly or through a reflector, with the geometrical arrangement being such that the radiation passes through the optically transmissive medium at least once on its path between the radiation source and the radiation detector. In this arrangement the distance covered within the optically transmissive medium can be dependent on the angle of inclination, so that the radiation detector receives a greater or lesser amount of radiation depending on the inclination angle. Also with an optically transmissive measurement it is possible to unite the functions of the radiation emitter and radiation receiver in a single component, for example, in a reflected light barrier adapted to be arranged on one side of a pendulum or the like, or a bifurcated light barrier in which transmitter and receiver can be disposed on opposite sides of the transmissive medium. The possibility also exists to direct the radiation in such manner that it is passed through the optically transmissive medium several times whereby an improved signal-to-noise ratio is obtainable under circumstances.

Preferably, the optical devices referred to in the foregoing are encapsulated in a manner essentially impervious to radiation, thereby preventing the measurement from being affected by stray light or spurious radiation. When provision is made for a reflector in the radiation path between the radiation source and the radiation detector for deviation, this reflector may be formed by an appropriate surface section of an in particular optically radiation-impervious housing surrounding the arrangement. In cases where the housings or enclosures are not impervious to radiation, provision is made for a device for the compensation of residual light. This device enables the same radiation sources and radiation detectors to be employed, with the residual light compensation taking place by (electronic/optical) subtraction of reflections at two different radiation intensities.

It is also possible to utilize the transmission and/or reflection of waves for implementing an acoustically operating inclination sensing device operating with ultrasound, for example.

The optically or acoustically operating inclination sensing devices described are the preferred approach, among other reasons also because the cooperative relationship between the sensing elements can take place in non-contacting fashion and free from reaction forces. As far as forces are concerned, this enables the gravity-induced adjustment of the equilibrium of the positioning element to proceed in a manner completely unaffected by the processes used for measurement of the inclination angle. Furthermore, sealing problems as they occur with electrolyte sensing devices can be eliminated. The devices have a practically unlimited service life and are able to operate largely without wear.

The inclination sensing device may also be configured as a capacitive inclination sensing device in which the sensing elements may act as cooperating charge carrier surfaces. The inclination signal is obtainable from an inclination-angle-dependent variation of the surface dimension of the capacitor formed by the sensing elements and/or from a variation of the relative distance of the cooperating charge carrier surfaces. In one embodiment of a capacitive inclination sensing device the positioning element is configured as a rolling member movable preferably in one axis and designed to roll off along a preferably uniaxially curved rolling surface of the inclination sensing device, wherein the inclination signal occurs in dependence upon the position of the rolling member relative to the rolling surface. At least one charge carrier surface of the inclination sensing device can be associated with the rolling surface, with preferably the width of the charge carrier surface transverse to the direction of motion or direction of rolling of the rolling member varying preferably linearly, for which purpose the charge carrier surface may be of a wedge-type or trapezoidal configuration, for example. An advantageous embodiment of this type is described in connection with the embodiments.

The possibility also exists to provide an inductively operating inclination sensing device in which, for example, one sensing element, in particular a part of the positioning element, is configured as an element guiding the magnetic flux. The other sensing element may include at least one electric coil which preferably surrounds a core made of a magnetizable material for guiding and amplifying the magnetic flux. Together with the element guiding the magnetic flux, the coil arrangement may form an essentially closed magnetic circuit, wherein the magnetic resistance of the magnetic circuit may be dependent on the inclination angle. The sensing elements may cooperate in non-contacting fashion, which is accomplished by an air gap maintained between the coil arrangement curved, for example, in a horseshoe-shaped or circular-arc shaped configuration, meaning its core and the element guiding the magnetic flux. The electromagnetic interaction between the sensing elements can be utilized to advantage in the manner of an eddy-current brake to effect damping of the normally oscillating motion of the positioning element as it moves into its rest position.

The generation of electrical inclination signals possible according to the invention affords a plurality of advantageous possibilities of further processing of the inclination signal, which result in optimal maneuverability of the device and an enhanced measurement accuracy in the determination of blood pressure. The movable positioning element provided in the inclination detecting device which is configured in the manner of a pendulum or as a rolling member, for example, has a characteristic oscillatory response characterizable by a natural frequency. Depending on the way the patient moves, adoption of the measuring position involves exciting the positioning element into oscillating with a more or less high initial amplitude. This oscillation dies down gradually until adjustment of the equilibrium, which may require a prolonged period of time when the oscillation is undamped. Damping of the oscillation of the positioning element is possible actively by means of oil damping, for example. Proceeding from a computed or experimentally determined oscillatory response of the oscillation system comprising the positioning element, the generation of an electrical inclination signal advantageously enables the determination of an estimated value for the position of equilibrium of the positioning element, and hence for the gravity vector, electronically or by computation from a damped inclination signal varying periodically upon a change in inclination, also when the position of equilibrium has not been adopted as yet. In contrast to mechanical solutions, there is hence no need to wait with the reading until the positioning element has died down. For determination of the estimated value, an adaptive electronic filtering of the inclination signal varying periodically during dying-out can be performed.

Depending on the purpose for which the inclination signal is to be used it is also possible to resort to the speed or acceleration of the positioning element, which is possible, for example, by generating the first or second time derivative of the inclination signal electronically or by computation. On the basis of the motion or acceleration of the measurement device or the subject's limb thereby derivable, it can be established whether the subject is generally at sufficient ease to be able to perform a meaningful measurement. If an increased degree of motor activity is detected so that the blood pressure reading is possibly not representative, the measurement can be aborted and/or a visual or audible warning of the inaccurate reading can be given. Dynamic errors, also referred to as motion artifacts which are attributable to tremor or an uncontrolled arm movement, are thereby avoidable or at least determinable.

The electrical inclination signal also affords an easy possibility of correcting a measured blood pressure value in accordance with the detected inclination and delivering a value which corresponds to a measurement made at the level of the heart. A preferred feature is the provision of a user guidance explained by way of example in connection with the embodiments, which is intended to guide the subject's arm to an appropriate position prior to the blood pressure measurement cycle. This enables the electronic evaluating device to be of particularly straightforward construction, in addition to achieving a training effect for the user. Furthermore, an advantageous arrangement and/or configuration of a display device described in connection with the embodiments, which is essentially readable only when the subject's wrist is held against the upper body part at about the level of the heart, serves to enhance the reliability and repeatability of the blood pressure measurements. Motion artifacts can be reduced and the user can be made aware of the level of his or her heart.

These and further features will become apparent not only from the claims but also from the description and the accompanying drawings, and it will be understood that the individual features, whether taken alone or combined in the form of sub-combinations, may be implemented in an embodiment of the invention and in other fields and represent advantageous embodiments.

An embodiment of the invention is illustrated in the accompanying drawings and will be explained in greater detail in the following. In the drawings, FIG. 1 is a view of a subject carrying an embodiment of a blood pressure monitoring device of the invention at his wrist, and an enlarged view of the visual display with user guidance disposed on the narrow side of the wrist;

FIG. 5 is an oblique perspective top plan view of a capacitively operating inclination detecting device showing the housing lid removed; and FIG. 6 is an oblique perspective bottom plan view of the inclination detecting device shown in FIG. 5.

Figure 1:
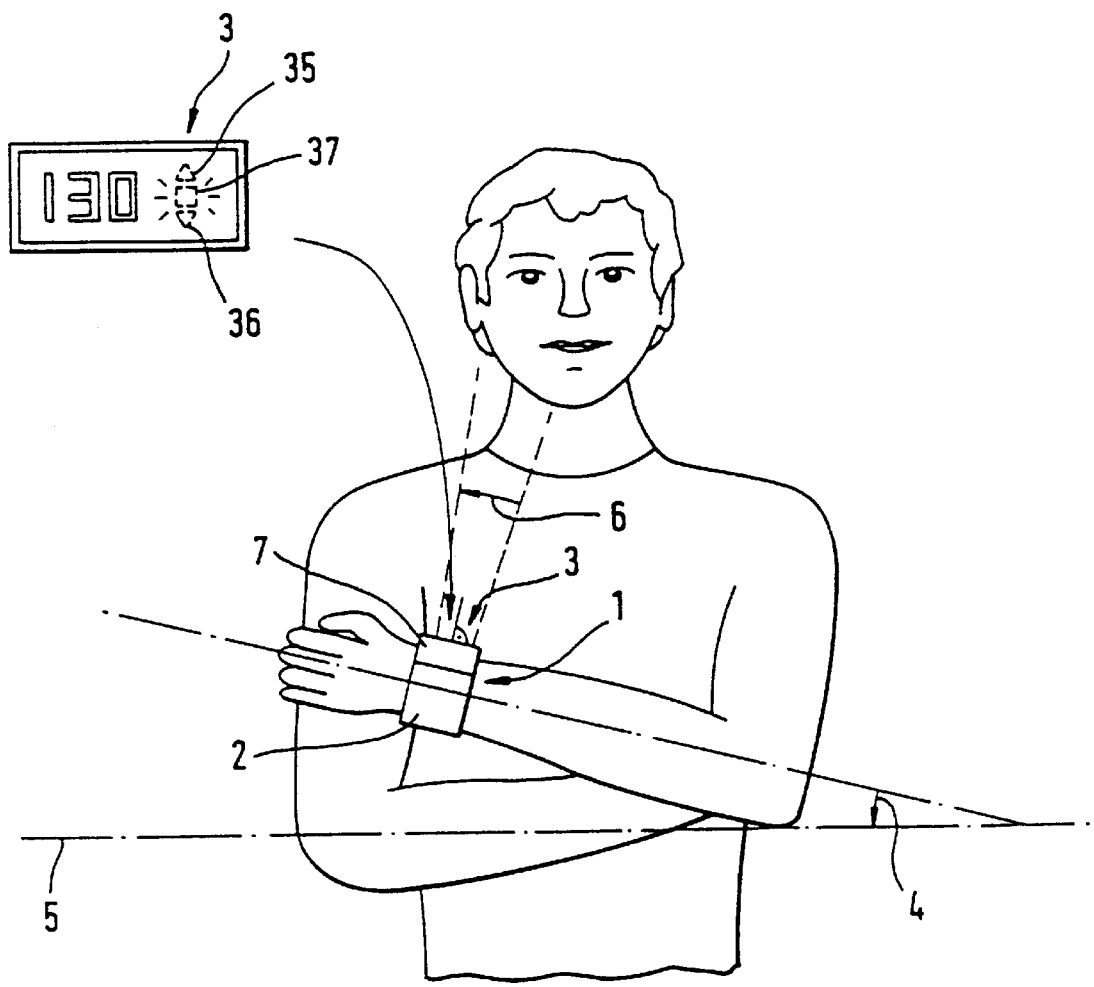

The subject shown in FIG. 1 carries a wrist blood pressure monitoring device 1 in the region of his left or right wrist, the device having as applicator unit a cuff to be wrapped around the wrist to enable a pressure sensor to be applied against the inside of the wrist for signal pickup. The sensor may be of the capacitive or piezoresistive type, for example. The cuff has an integrally formed bladder inflatable preferably by air using a pumping device, by means of which bladder the blood circulation through the arteries in the interior area of the wrist can be occluded by exertion of a suitable pressure. During the deflation cycle, the diastolic and the systolic blood pressure and, where applicable, the mean blood pressure and/or the pulse can be determined in a manner known in the art, as by means of the oscillometric methodology. Integrated into the housing of the blood pressure monitoring device are the pumping device, a deflation valve, the pressure sensor, a display device 3, a control unit, a source of power supply and an inclination detecting device. The cuff is fixedly connected with the housing.

For a visual display of the measured values provision is made for the display device 3 which, with the blood pressure monitoring device properly applied, is situated in the region of the narrow side of the wrist close to the thumb, that is, along the cuff circumference in an about 90° offset relation to the bladder. With the arm in the position illustrated in FIG. 1 which is particularly well suitable for measurement and in which the lower arm is upwardly angled at an about 33° angle of inclination 4 relative to the horizontal 5 and the left hand grips the right upper arm, the LCD of the display device 3 shown top left in plan view faces the subject's head directly, so that the viewer's eye hits the display about vertically. The display can be configured such that it is essentially readable only when the arm is in the proper position shown. This is accomplishable, for example, by providing the display with a very small viewing angle 6 of, for example, 33°±5° or up to ±10° relative to the display area normal, as a result of which the user will not be able to read the display unless the viewing direction is within this particular solid angle. This alone already represents a user guidance prompting the user to hold the blood pressure monitoring device at about heart level and have the wrist rest against the upper body part. This is conducive to a particularly steady position of the arm without tremor or the like, and a corruption of measurement results attributable to such motion artifacts is avoided automatically.

The visual display 3 of the display device is arranged on the upper side of a housing 7 of the blood pressure monitoring device fixedly connected to the cuff. As recognizable in FIG. 2, fastened in the housing directly underneath the display at a position approximately parallel to the plane of the display is a printed circuit board or card 8 carrying the electronic components of the evaluating device and an inclination detecting device 10 explained in greater detail in the following.

Figure 3:
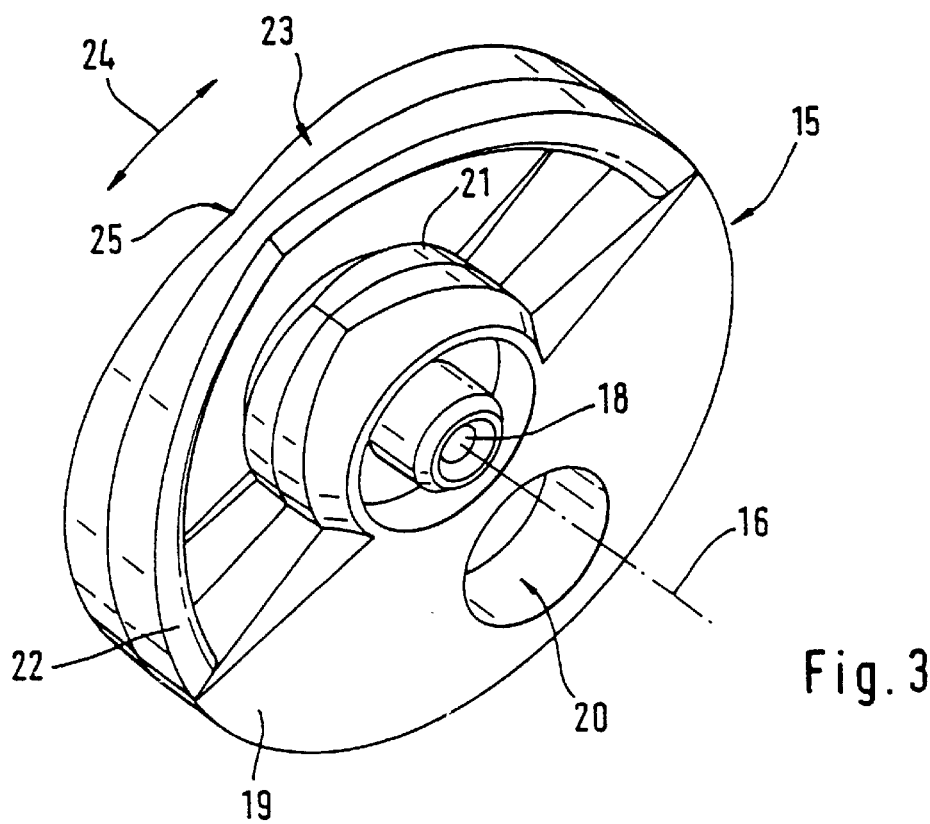
FIG. 3 is an oblique perspective top plan view of the rotary pendulum shown in FIG. 2.

The inclination detecting device 10 comprises a slim plastic housing 11 which is open at the top and the bottom and is attachable, by means of pins 12 integrally formed thereon and fitting into mating recesses 13 in the card 8, to the underside of the card facing away from the display without a tool being required. A positioning element in the form of a uniaxial rotary pendulum 15 shown particularly clearly in FIG. 3 is mounted in the housing 11 for rotation about an axis of rotation 16. For this purpose the housing 11 has on either side in the area of lateral protuberances 17 in the housing wall a downwardly open receptacle permitting a shaft introduced through the central axial opening 18 of the pendulum to be inserted from below with a snap action.

Figure 2:
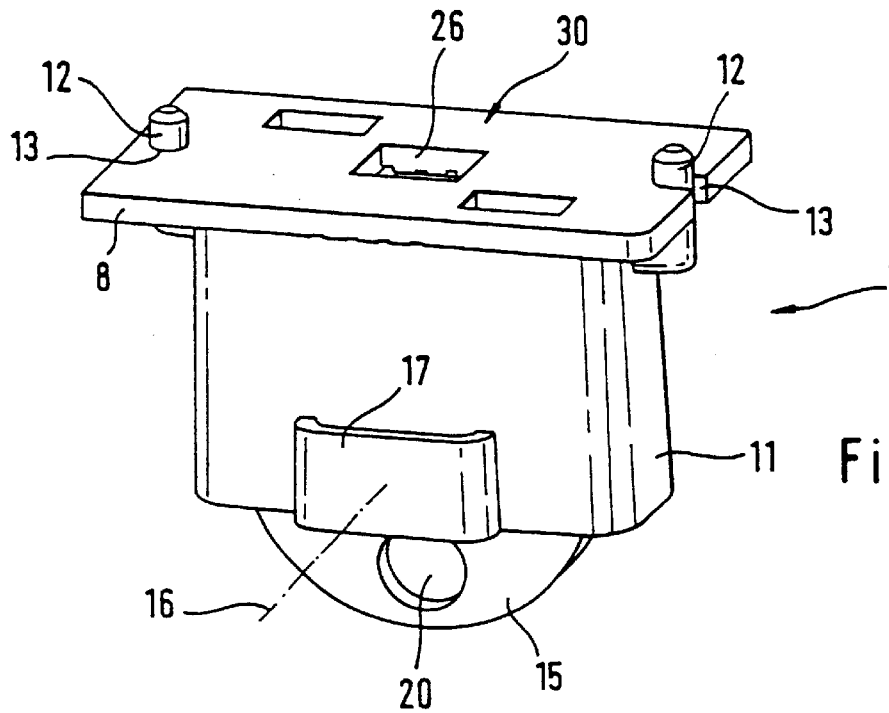
FIG. 2 is an oblique perspective view of part of an inclination detecting device provided with a rotary pendulum.

The pendulum 15 which is of circular shape in axial view comprises a single-piece plastic pendulum body with a solid, semicircular pendulum lower part 19 having a central, circular receiving opening 20 suitable for snapping engagement with a metal ball or the like for displacing the center of gravity of the pendulum to a location far outside the axis of rotation 16. The other half of the pendulum body is formed by an inner arc section 21 arranged concentrically with the axis of rotation 16 and an outer arc section 22 extending at a radial relative distance along the outer periphery of the pendulum. This outer arc section forms an arch encompassing an angle of about 180° and has a circular cylindrically curved, radial outer surface or peripheral surface 23 concentric with the axis of rotation 16. Its width perpendicular to the circumferential direction, meaning parallel to the axis of rotation 16 varies continuously in the arc direction 24 (in the embodiment shown the width varies linearly), said width variation being symmetrical to a zero position 25. The zero position 25, which is the point where two converging arc sections meet by tapering from the pendulum lower part to the zero position in a wedge-shaped configuration to about one fourth of their maximum axial width, lies diametrically opposite to the pendulum's center of gravity, said center of gravity being arranged on the straight line drawn between the axis of rotation 16 and the center of the receiving opening 20 and, with the metal ball inserted, being in close proximity to said center. With the pendulum inserted in the housing 11 as shown in FIG. 2, the pendulum's outer surface 23 lies directly underneath the card 8 and is accessible and visible through a central rectangular window 26 in the card, the zero position 25 lying in the center of the window 26 and being congruent with the optical axis of the reflected light barrier when the card is in the horizontal position.

In this embodiment, the outer surface 23 of the pendulum 15 fabricated from a light, in particular white plastics material serves as a movable sensing element, formed by part of the pendulum, that is, by the outer surface 23 of the outer arc section, of an optically reflectively operating inclination sensing device 30. The other sensing element cooperating therewith and fixed to the housing and being movable together with the housing of the blood pressure monitoring device comprises a reflected light barrier not shown (see the embodiment of FIG. 4) which is secured or securable to the card 8 in the area of the window 26. The term "light barrier" refers to the construction, related to a light barrier, of the inclination sensing device 30 comprised of radiation source and radiation receiver, irrespective of how the signals are further used at the radiation receiver. The light barrier comprises a radiation source in the form of a light-emitting diode directed at the outer surface 23 of the pendulum 15, and a photodiode or a phototransistor serving as radiation detector fitted to the same component directly adjacent thereto and having incident on it the optical radiation of the light-emitting diode diffusely reflected from the reflecting surface 23. In this arrangement the dimensioning and relative alignment of these elements are such that the intensity of the reflected optical radiation, meaning the amount of reflected radiation, depends significantly on the axial width of the portion of the arc section 23 lying in the area of the window 26. Thus, for example, with the card horizontally aligned, the amount of optical radiation reflected from the narrow area in close proximity to the zero position is only half the amount that is reflected when the card is inclined at an angle of about 45°, because on account of the wedge-shaped configuration of the arc section 22 in the area of the zero position 25 the width of the outer surface 23 is only half the width that would be present with the card in a position circumferentially offset through 45°. Because the converging trapezoidal or wedge-shaped surfaces 23 are symmetrical relative to the zero position 25, the same amount of reflected intensity results, irrespective of the direction of inclination, so that the inclination detection functions alike, whether the blood pressure monitoring device is fitted to the left or to the right wrist.

The inclination detecting device which affords economy of manufacture and assembly readily and without the aid of tools delivers at the output of the light barrier an electrical inclination signal which is suitable for ready evaluation and is strongly, ideally linearly, dependent on the angle of inclination. Thanks to the non-contacting and force-free cooperative relationship of the sensing elements, the adjustment of the equilibrium of the pendulum is in no way impeded or impaired by the sensor arrangement. The inclination detecting device is mountable directly on the printed circuit board 8, in particular essentially on its underside facing away from the display, which enables a particular compact construction of the blood pressure monitoring device, so that a simple fastening on the one hand and an electrical connection between the inclination sensing device and the card on the other hand are accomplished.

As an alternative or addition to the outer arc surface 23, it would also be possible to use for signal generation the outer surface of the inner arc section 21 which likewise tapers symmetrically in a wedge-shaped configuration. To compensate for systematic nonlinearities of the signal evaluating unit, a suitable embodiment provides for the outer arc surface to have correspondingly conformed and accordingly nonlinear or continuous forms or widths, that is, the geometry of the inclination sensing device compensates for the systematic nonlinearities. A pendulum essentially identical in form, in which the outer arc section 22, for example, is fabricated from a material transparent to visible light, being where applicable slightly opalescent, can be employed for an optically transmissive measuring system in which radiation passes through the three-dimensional arc section 22 in a direction parallel to the axis of rotation 16, for example. Depending on the rotary position of the pendulum, the length of the penetrated area and hence the respective intensity passed therethrough differ in magnitude, which effect can be utilized for the generation of an inclination signal. For example, when the outer surface 23 is constructed as a charge carrier surface by metallization, it is possible, in cooperation with a further charge carrier surface arranged, for example, in the window 26 at a small distance to the peripheral surface 23, to provide a capacitive sensor whose capacitance is a function of the rotary position of the pendulum 15 and hence of the respective angle of inclination in a linear or some other functional way. When the outer surface 23 is not concentric with the axis of rotation, extending instead spirally with a circumferentially varying radial distance to the axis of rotation, an inclination-angle-dependent variation of the distance between the sensing elements is accomplishable which is suitable for evaluation by measuring the capacitance, for example.

In the embodiment shown and the embodiments subsequently described, the electrical inclination signal is used for the avoidance of measurement errors resulting from improper positioning by providing for interactive user guidance on the basis of the inclination signal. This includes the step of supplying the user with suitable visual signals on the display device 3 of the blood pressure monitoring device until the lower arm position determining the angle of inclination is within a predetermined angular tolerance range around a reference angle which, where applicable, is predeterminable for the particular subject, being where applicable individually adjustable. The blood pressure monitoring device 1 is then in a measuring position so close to the level of the heart that hydrostatically induced measurement errors are precluded or negligible. The need to correct measured values is obviated. The visual signal the user receives as guidance towards an optimum measuring position can be given at the beginning of and/or during the pressure measurement cycle. In the given example the display device 3 has an upwardly directed arrow 35, a downwardly directed arrow 36 and a square field 37 disposed in between. For example, the upwardly directed illuminated arrow 35 may light or flash in red prompting the user to move his or her wrist in upward direction to occupy the proper measuring position. The display field 37 which may be green, for example, may light up when the proper measuring position is reached. A user guidance in the form of a red light for an improper measuring position and/or a green light for a correct measuring position and/or an audible warning signal for an improper measuring position and/or "OK" signal for a proper measuring position may also be contemplated. It can also be considered that the visual display of the measured value is not activated until an appropriate measuring position is established.

Figure 4:
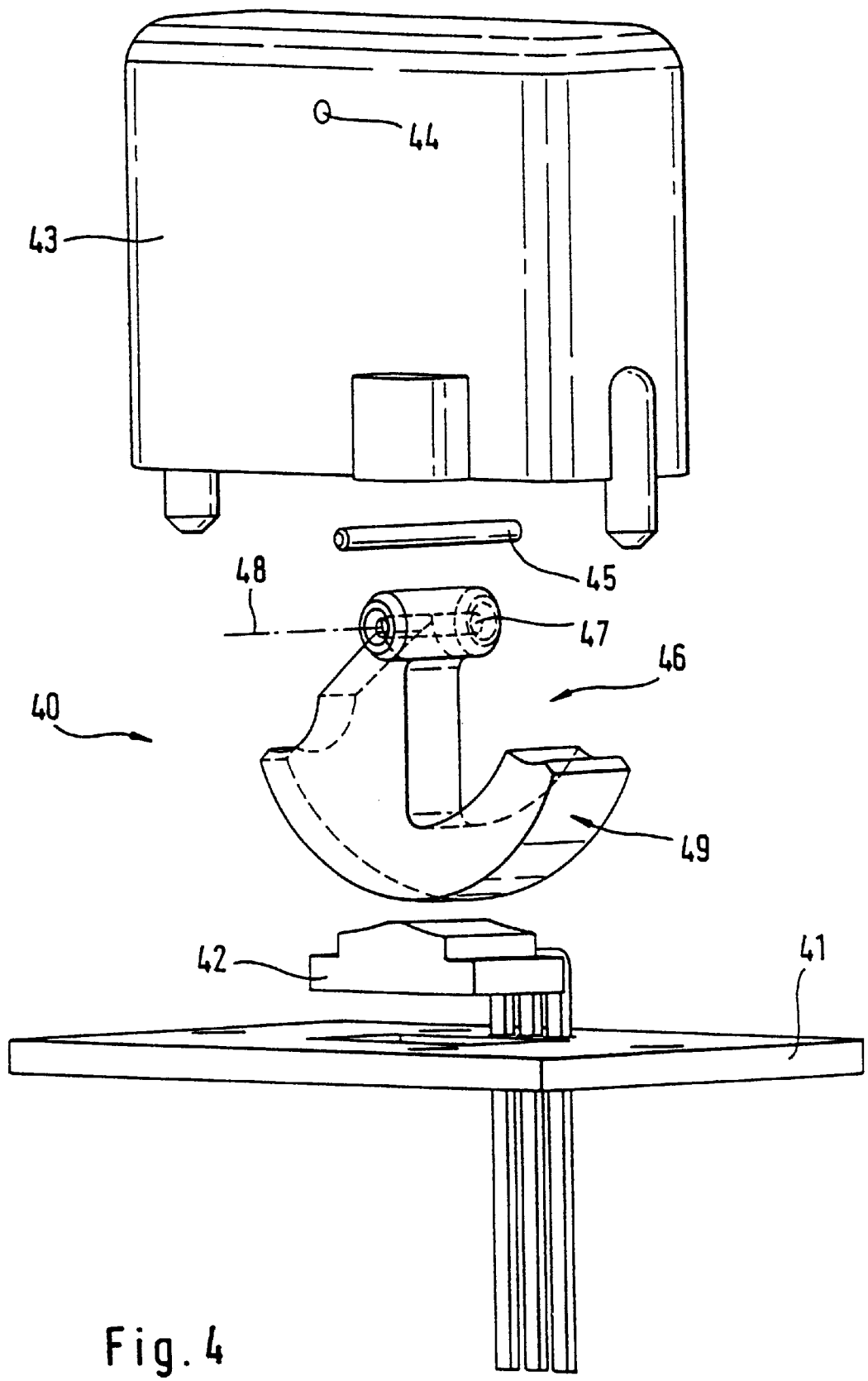
FIG. 4 is a perspective exploded view of another embodiment of an optically reflectively operating inclination detecting device.

FIG. 4 shows another embodiment of an optically reflectively operating inclination sensing device 40. Mounted on a printed circuit board or card 41 is a reflected light barrier 42 forming the sensing element of the device, which is fixedly mounted on the housing. Above the sensing element is a plastic cover 43 having its upper end closed and its lower end open and being securable to the narrow ends of the card 41 by means of pins. Provided in the upper area of the cover on its broad dimension are bores 44 arranged in relative alignment for mounting a pivot or shaft 45 insertable through the bores 44. The pivot 45 serves to rotatably mount a positioning element 46 configured as a rocker or pendulum disposed in the interior of the cover above the light barrier 42 when the device is in assembled condition, said positioning element having in a hub section thereof a passage bore 47 for the pivot 45. When suspended, the rocker 46 integrally formed of a light plastics material is able to oscillate about an axis of rotation 48 formed by the central axis of the bore 47 and has a circumferential surface 49 concentric with said axis of rotation and curved about said axis in a circular cylindrical configuration, describing a circumferential angle of between about 90° and 120° and, thanks to its wedge shape, possessing a width decreasing or increasing linearly in the peripheral direction, roughly doubling in width from the one to the other end.

In the position of rest with the printed circuit board in horizontal position, the trapezoidal or wedge-shaped circumferential surface 49, which forms the one sensing element of the sensing device, is roughly in the position shown due to the position of the center of gravity, being centered above the reflected light barrier 42 which serves as the other sensing element. A section of medium width of the reflecting surface 49 lies opposite the light barrier at a small relative distance without making contact therewith. When the blood pressure monitoring device with its sensing device experiences a forward or backward tilt (about an axis parallel to the axis 48), owing to its wedge shape the diffusely reflecting surface 49 of the rocker becomes correspondingly greater or smaller in the area of the light barrier 42 covering the maximum overall width of the reflecting surface. The effect thereby achieved is that the quantity of reflected optical radiation either increases or decreases in correspondence with the width of the reflecting surface relative to the horizontal position. By detecting the reflected radiant intensity by means of a radiation detector of the light barrier 42 an electrical inclination signal is hence producible at the light barrier output, from which signal both the amount of inclination, that is, the absolute angle, and the direction of the inclined position are derivable.

A possibility of producing an electrical inclination signal electrically capacitively will be explained with reference to FIGS. 5 and 6. This inclination detecting device 50 comprises a plastic housing lower part 51 to which a cap-shaped plastic housing upper part 52 can be snap-fitted using tabs at the respective ends of the upper part 52 which engage with cooperating detent noses at the respective ends of the lower part. As this occurs, two pins provided at the narrow ends of the housing lower part engage into mating bores in the upper part to locate the housing parts centrally and provide a safeguard against relative rotation. The lower part has a concave cylindrical inner side curved in a circular-arc-shaped configuration onto which two identical metal wedges 53 tapering in wedge shape are placed parallel to each other and at a relative spacing. Each of the metal wedges has on its free upper side a free surface 54 curved in a circular cylindrical configuration, narrowing and widening in the direction of the curvature. Provided on the opposite undersurface is a respective contact pin 55 extending through the bottom of the housing lower part. A metal roll 56 disposed in the interior of the housing with the device in assembled condition comprises a circular-cylindrical body 57 having a disk-shaped circumferential shoulder 58 of greater diameter formed thereon centrally. The running surfaces of the roll formed by the cylindrical body sections on either side of the shoulder 58 are provided with a thin varnish coating for electrical insulation. The circumferential shoulder of the roll runs in a guide slot 59 provided on the housing lower part between the metal wedges 53 and serves to guide of the roll 56 laterally as it rolls off along the metal wedges 53. Integrated into the cover 52 are two parallel supports 60 shaped in the manner of a circular arc with a curvature corresponding to the curvature of the surfaces 54, to prevent the roll 56 from unseating itself from the metal running surfaces 56.

The metal wedges 53 serve as sensing elements of the sensing device attached to the housing, their free surfaces 54 functioning as running surfaces and charge carrier surfaces. The rolling member formed by the roll 56 serves as positioning element, with the outsides of the cylinder body 57 facing the insulation forming equally charge carrier surfaces, meaning sensing elements of the capacitive sensor. The capacitance of the sensor is determined essentially by the position of the rolling member 56 on the running surfaces 54 and is substantially a function of the axial length of the practically linear contact area between the roll and the metal wedges.

In the position of rest the roll 56 lies, for example, approximately centrally between the ends of the metal wedges on the curved surfaces 54, and an initial capacitance prevails. On tilting the inclination detecting device in forward or rearward direction, the rolling member 56 rolls forward or rearward correspondingly on the curved surfaces. As this occurs, the portion of the wedge-shaped surfaces 54 making rolling contact with the rolling member becomes greater or smaller in dependence upon the angle of tilt, causing the capacitance of the sensor to increase or decrease correspondingly. The capacitance of the sensing device 50 can then be determined by means of an evaluating device connected via the contact pins 55. The direction and the degree of tilt of the inclination sensor or the distance the roll has traveled are derivable from the capacitance.

Numerous variants of blood pressure monitoring devices of the invention are possible. Thus any type of display as also employed with portable computers can be used as visual display devices including, for example, LCDs of the TN, STN, DSTN, TFT or any other type.

According to a further embodiment the blood pressure monitoring device includes an adjusting device enabling the range of inclination to be adjusted.

What is claimed is:

1. A blood pressure monitoring device, comprising:
   a housing;
   a display that displays an inclination of the blood pressure monitoring device, the display being attached to the housing;
   a pressure sensor that detects a pressure; and
   an inclination detector that detects the inclination of the blood pressure monitoring device and for transmitting an inclination signal indicative of the inclination, the inclination detector including
      a moveable positioning element rotatably fixed to the housing;
      a first sensing element fixed to the positioning element, the first sensing element including an arc section having at least one variable property; and
      a second sensing element fixed to the housing, the second sensing element positioned proximate to the arc section of the first sensing element, the first and second sensing elements being in communication with one another;
   wherein the inclination signal is derivable as an absolute signal from the position of the first sensing element relative to the second sensing element.

2. The blood pressure monitoring device of claim 1 wherein the arc section is of a width variable in the direction of arc.

3. The blood pressure monitoring device of claim 1, wherein the arc section has a surface property variable in the direction of arc.

4. The blood pressure monitoring device of claim 3, wherein the arc section has a linearly variable surface property.

5. The blood pressure monitoring device of claim 3, wherein the arc section has an optical reflecting property variable in the direction of the arc.

6. The blood pressure monitoring device of claim 1, wherein the arc section is configured in the direction of arc such that a distance from the arc section to the second sensing element varies in dependence upon the angle of inclination.

7. The blood pressure monitoring device of claim 6, wherein the distance between the arc section and the second sensing element varies linearly in dependence upon the angle of inclination.

8. The blood pressure monitoring device of claim 1, wherein the first sensing element is of a wedge-shaped or trapezoidal configuration at least in sections thereof.

9. The blood pressure monitoring device of claim 1, wherein the sensing elements cooperate in non-contacting fashion.

10. The blood pressure monitoring device of claim 1, wherein the sensing elements cooperate free from reaction forces.

11. The blood pressure monitoring device of claim 1, wherein the first sensing element makes contact with the second sensing element.

12. The blood pressure monitoring device of claim 1, wherein the variation of a property of the arc section related to the direction of arc proceeds symmetrically relative to a zero position, the zero position corresponding to a horizontal alignment of the blood pressure monitoring device.

13. The blood pressure monitoring device of claim 1, wherein the positioning element is of a pendulum-type configuration and fixedly mounted on the housing for rotation about an axis, and wherein the arc section of the first sensing element is arranged essentially concentrically with the axis of rotation.

14. The blood pressure monitoring device of claim 1, wherein the first sensing element is configured as a curved roll-off surface with one axis and the second sensing element is provided on a rolling member forming the positioning element, the first and second sensing elements cooperating with one another.

15. The blood pressure monitoring device of claim 1, wherein the sensing elements are arranged essentially underneath the display.

16. The blood pressure monitoring device of claim 15, wherein the display includes a card, and wherein the sensing elements are attached to an underside of the card.

17. The blood pressure monitoring device of claim 1, wherein the first sensing element includes at least one reflecting surface for optical radiation while the second sensing element includes at least one source of radiation and at least one radiation detector, wherein the reflecting surface is aligned relative to the radiation source and the radiation detector such that optical radiation from the radiation source which is reflected by the reflecting surface is incident on the radiation detector.

18. The blood pressure monitoring device of claim 17, wherein the radiation source and the radiation detector are integrated in a common component configured as a light barrier.

19. The blood pressure monitoring device of claim 1, wherein the first sensing element includes an optically transmissive medium while the second sensing element includes at least one source of radiation and at least one radiation detector, the optically transmissive medium being arranged in relation to the radiation source and the radiation detector such that optical radiation from the radiation source is incident on the radiation detector, passing through the optically transmissive medium.

20. The blood pressure monitoring device of claim 19, wherein the optical radiation passes through at least one reflecting surface.

21. The blood pressure monitoring device of claim 19, wherein the radiation source and the radiation detector are integrated in a common component configured as a light barrier.

22. The blood pressure monitoring device of claim 1, wherein the first and second sensing elements are encapsulated in a manner essentially impervious to radiation.

23. The blood pressure monitoring device of claim 1, wherein the sensing elements are cooperating charge carrier surfaces of a capacitive inclination sensor, the sensing elements being electrically insulated from each other.

24. The blood pressure monitoring device of claim 1, wherein the inclination detector is an acoustic inclination sensor.

25. The blood pressure monitoring device of claim 1, wherein the inclination detector is an inductive inclination sensor in which the first sensing element is configured as an element guiding a magnetic flux, the first sensing element being a part of the positioning element, and the second sensing element includes at least one electric coil arrangement the coil arrangement, in combination with the element guiding the magnetic flux, forming an essentially closed magnetic circuit.

26. The blood pressure monitoring device of claim 25, wherein the coil arrangement includes a core made of a magnetizable material.

27. The blood pressure monitoring device of claim 1, further comprising an evaluating unit that determines an equilibrium inclination signal which, in response to an oscillatory response of the positioning element, uses a damped inclination signal varying periodically upon a change in inclination to derive an estimated value for an equilibrium position of the positioning element corresponding to inclination of the monitoring device.

28. The blood pressure monitoring device of claim 1, wherein the display is a visual display which, with the blood pressure monitoring device properly applied about a wrist, is positioned on a narrow side of the wrist and has a display area oriented essentially parallel to said narrow side.

29. The blood pressure monitoring device of claim 1, wherein the display is a visual display device configured such that the display is essentially readable by a wearer upon whose arm the device is properly mounted only when the arm is in a desired position for blood pressure monitoring.

30. The blood pressure monitoring device of claim 29, wherein the display has a viewing angle between about 23 and 43 degrees relative to normal.

31. The blood pressure monitoring device of claim 30, wherein the display has a viewing angle between about 28 and 38 degrees relative to normal.

32. The blood pressure monitoring device of claim 1, wherein the display includes feedback indicators that provide a user with feedback on whether accurate measurement conditions have been achieved.

33. The blood pressure monitoring device of claim 32, wherein the feedback indicators are arrows pointing in opposite directions.

* * * * *